United States Patent [19]

Stürmer et al.

[11] Patent Number: 5,723,642
[45] Date of Patent: Mar. 3, 1998

[54] OPTICALLY ACTIVATE PHOSPHINES, THEIR PREPARATION AND THEIR METAL COMPLEXES, AND USE IN ASYMMETRIC SYNTHESIS

[75] Inventors: Rainer Stürmer, Roedersheim; Lothar Laupichler, Heidelberg; Paul Knochel; Falk Langer, both of Marburg, all of Germany

[73] Assignee: BASF Aktiengesellschaft, Ludwigshafen, Germany

[21] Appl. No.: 643,586

[22] Filed: May 6, 1996

[30] Foreign Application Priority Data

May 12, 1995 [DE] Germany ............ 195 169 68.9

[51] Int. Cl.$^6$ .................................. C07F 9/02
[52] U.S. Cl. .............. 556/18; 556/20; 556/136; 568/8; 568/12; 568/17
[58] Field of Search .............. 556/18, 20, 136; 568/8, 12, 17

[56] References Cited

FOREIGN PATENT DOCUMENTS

| | | |
|---|---|---|
| 151 282 | 8/1985 | European Pat. Off. . |
| 185 882 | 7/1986 | European Pat. Off. . |
| 269 395 | 6/1988 | European Pat. Off. . |
| 271 311 | 6/1988 | European Pat. Off. . |
| 614 901 | 9/1994 | European Pat. Off. . |

OTHER PUBLICATIONS

Kagan, *Asymmetric Synthesis* vol. 5, pp. 13–23, 1985.
Tani et al., *J. Am. Chem. Soc.*, vol. 106, pp. 5208–5217, 1984.
Noyori, *Acc. Chem. Res.*, vol. 23, 1990, pp. 345–350.

*Primary Examiner*—Profirio Nazario-Gonzalez
*Attorney, Agent, or Firm*—Keil & Weinkauf

[57] ABSTRACT

Optically active phosphines of the general formula I or II

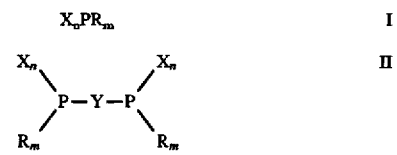

where the variables have the following meanings:

X is an optically active terpene radical,

R is an unsubstituted or substituted phenyl radical,

Y is a bridge member having 1–10 C atoms in the formula I n is 1,2 or 3 and m is 0,1 or 2 with the proviso that n+m=3 in the formula II n is 1 or 2 and m is 0 or 1 with the proviso that n+m=2, their preparation and use are described.

11 Claims, No Drawings

OPTICALLY ACTIVATE PHOSPHINES, THEIR PREPARATION AND THEIR METAL COMPLEXES, AND USE IN ASYMMETRIC SYNTHESIS

The present invention relates to optically active phosphines, a process for preparing optically active phosphines and their metal complexes, and the use of the metal complexes for enantioselective hydrogenation, hydroformylation and isomerization.

Enantioselective hydrogenation and isomerization using rhodium and ruthenium complexes play an important part in the synthesis of optically active compounds (eg. Tani et al. J. Am. Chem. Soc. 106 (1984), 5211; R. Noyori, Acc. Chem. Res. 23 (1990), 345. The catalysts used here, which are usually prepared from an optically active diphosphine ligand and a rhodium or ruthenium compound, are very expensive and only accessible by complicated preparation processes.

The known preparation methods for optically active phosphines have, without exception, many stages and usually comprise a technically complicated and expensive resolution (eg. EP-A 614901; EP-A 271311; H. B. Kagan, "Chiral Ligands for Asymmetric Catalysis" in Asymmetric Synthesis, Vol. 5 (1985), pages 13–23, EP-A 151282; EP-A 185882; R. Noyori, Acc. Chem. Res. 23 (1990), 345; EP-A 269395). The industrial utilization of such catalysts therefore is usually uneconomical.

It is an object of the present invention to provide optically active phosphines which are suitable as ligands for transition metal complex catalysts, in whose preparation the disadvantages indicated above are avoided.

We have found that this object is achieved by a process for preparing optically active phosphines, which comprises
a) hydroborating an optically active olefin in a known manner,
b) reacting the reaction product from step a) with a dialkylzinc compound,
c) reacting the reaction product from step b) with a phosphorus halide to give the phosphine.

The hydroboration of olefins according to step a) is known (eg. Cragg, Organoboranes in Organic Synthesis, Marcel Dekker, NY, 1973).

Preferably, in step a) terpenes, in particular the optically active compounds (+)-alpha-pinene, (−)-alpha-pinene, (+)-beta-pinene and (−)-beta-pinene, (+)-delta2-carene, (+)-delta3-carene, (+)-menthene, (+)- and (−)-camphene, (+)-fenchene, (+)- and (−)-limonene, (+)-menthadiene and (+)-longifolene are reacted with borane in the form of its dimethyl sulfide, tetrahydrofuran, ether or amine adducts in order to obtain the trialkyl-, dialkyl- or monoalkylborane.

The reaction product from step a) is then reacted with a dialkylzinc compound, preferably dimethyl-, diethyl- or di-n-octylzinc, in order to obtain the corresponding organozinc compound containing the abovementioned terpene radicals (step b)).

The reaction product from step b) is reacted with a phosphine which carries one or more leaving groups. Suitable leaving groups are particularly halogen radicals, in particular chlorine radicals.

Particularly preferred phosphines of this type are phenylphosphorus dichloride, diphenylphosphorus chloride, phosphorus trichloride, phosphorus tribromide, phosphorus triiodide, 1,2-bis(dichlorophosphino)ethane, 1,3-bis(dichlorophosphino)propane and 1,4-bis(dichlorophosphino)butane.

After addition of borane in the form of its dimethyl sulfide, tetrahydrofuran, ether or amine adduct, the phosphine sought is isolated in the form of its borane adduct. The respective phosphine can be liberated from this adduct by heating with a low-boiling amine, preferably with ethylamine, dimethylamine, ammonia, methylamine, trimethylamine, triethylamine, propylamine and, particularly preferably, diethylamine.

The invention furthermore relates to optically active phosphines of the general formula I or II $$X_n PR_m \qquad \text{I}$$

$$\begin{array}{c} X_n \diagdown \qquad \diagup X_n \\ P-Y-P \\ \diagup \qquad \diagdown \\ R_m \qquad \qquad R_m \end{array} \qquad \text{II}$$

where the variables have the following meanings:

X is an optically active terpene radical,

R is an unsubstituted or substituted phenyl radical,

Y is a bridge member having 1–10 C atoms in the formula I n is 1,2 or 3 and m is 0,1 or 2 with the proviso that n+m=3 in the formula II n is 1 or 2 and m is 0 or 1 with the proviso that n+m=2.

The bridge member Y can consist of an unbranched or branched alkyl or arylalkyl chain. Unbranched alkyl chains having 1–6 C atoms, in particular ethane, propane and butane radicals, are preferred as Y.

Catalytically active complexes can then be synthesized from these novel phosphines in a known manner (eg. Uson, Inorg. Chim. Acta 73 (1983), 275, EP-A 0158875, EP-A 437690) by reaction with rhodium, iridium or ruthenium complexes which contain labile ligands (eg. [RuCl$_2$(COD)]$_n$, Rh(COD)$_2$BF$_4$, Rh(COD)$_2$ClO$_4$, [Ir(COD)Cl]$_2$, p-cymene-ruthenium chloride dimer).

The invention therefore also relates to transition metal complexes of the general formula III or IV $$\left[ \begin{array}{c} X \diagdown \diagup R \\ P \\ \diagdown \\ M \\ | \\ L_p \end{array} \right]^{q\oplus} DP^{\ominus} \qquad \text{III}$$

$$\left[ \begin{array}{c} X \diagdown \qquad Y \qquad \diagup X \\ \diagdown \diagup \qquad \diagdown \diagup \\ P \qquad \qquad P \\ \diagup \qquad | \qquad \diagdown \\ R \qquad M \qquad R \\ | \\ L_p \end{array} \right]^{q\oplus} DP^{\ominus} \qquad \text{IV}$$

where the variables X, Y, R, m and n have the abovementioned meanings and the other variables have the following meanings:

D is the equivalent of a noncoordinated anion,

L is an organic ligand,

M is a transition metal, p is 0 to 4 and q is 0 to 4.

M is preferably a metal from the group consisting of Ru, Rh and Ir.

The invention additionally relates to a process for preparing the abovementioned transition metal complexes, which comprises reacting a compound I or II in a manner known per se with a transition metal compound V

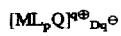

where Q is a leaving group.

The invention also relates to the use of the transition metal complexes III or IV as catalysts for asymmetric hydrogenation reactions, for asymmetric hydroformylation reactions and for the asymmetric isomerization of allylamines to enamines.

EXAMPLE 1

Preparation of (−)-1,2-bis(cis-dimyrtanylphosphino)ethane

Preparation of tri(cis-myrtanyl)borane 13.6 g (100 mmol) of (−)-(1S)-beta-pinene were cooled to −10° C. and treated in the course of 10 min with 2.28 g (30 mmol) of borane-dimethyl sulfide adduct. After 10 min, the suspension was diluted with 15 ml of ether and stirred for 2 h at 0° C. and for 8 h at room temperature. All volatile constituents were stripped off under reduced pressure. 12.6 g (99% yield) of tri(cis-myrtanyl)borane were isolated as a white solid.

1H-NMR (200 MHz, CDCl$_3$) d=0.81 (d, J=9.4 Hz, 3H), 0.98 (s, 9H), 1.09 (s, 9H), 1.32 (m, 9H), 1.55 (m, 3H), 1.80 (m, 12H), 2.15–2.45 (m, 6H)

Preparation of di(cis-myrtanyl)zinc 12.5 g (29.6 mmol) of tri(cis-myrtanyl)borane were suspended in 12 ml of hexane and cooled to 0° C. After addition of 6.0 ml (60 mmol) of diethylzinc, the mixture was stirred at 0° C. for 30 min. The hexane and excess diethylzinc were removed under reduced pressure by stirring for four hours at 40° C. 15.0 g (44.1 mmol) of di(cis-myrtanyl)zinc (99% yield) were obtained as a colorless oil.

1H-NMR (200 MHz, CDCl$_3$) d=0.61 (dd, J=7.5 and 9.0 Hz, 4 H), 0.86 (d, J=9.2 Hz, 2H), 1.10 (s, 6H), 1.21 (s, 6H), 1.34–1.53 (m, 2H), 1.70–2.19 (m, 10 H), 2.30 (m, 4H)

Preparation of (−)-1,2-bis(cis-dimyrtanylphosphino)ethane-bisborane Complex 0.46 g (2 mmol) of 1,2-bis(dichlorophosphino)ethane were added dropwise at 0° C. to a solution of 6.61 g (6.0 mmol) of di(cis-myrtanyl)zinc in 10 ml of THF. After addition was complete, the cooling bath was removed and the mixture was heated at 40° C. for 12 h. The reaction mixture was again cooled to 0° C. and treated with 6 ml (6 mmol) of a 1M solution of borane-dimethyl sulfide complex in methylene chloride. After 10 min at 0° C., the solvent was removed and the residue was flash chromatographed. 0.93 g of the phosphine-borane complex were isolated as a white solid. (Yield: 70%)

Melting point: 148° C., specific rotation: −38.2° (c=3.35 in chloroform). 1H-NMR (200 MHz, CDCl$_3$) d=0.9 (d, J=10.0 Hz, 4H), 0.99 (s, 12 H), 1.16 (s, 12 H), 1.35–1.55 (m, 4H), 1.60–1.96 (m, 28H), 1.96–2.20 (m, 4H), 2.20–2.40 (m, 8H)

Preparation of (−)-1,2-bis(cis-dimyrtanylphosphino)ethane 0.33 g (0.5 mmol) of (−)-1,2-bis(cis-dimyrtanylphosphino)ethane-bisborane complex were heated at 50° C. for 45 min after addition of 1 ml (10 mmol) of diethylamine. All volatile material was then removed at 0.1 mm Hg and the process was repeated again twice. 0.31 g (98% yield) of (−)-1,2-bis(cis-dimyrtanylphosphino)ethane were obtained as a white solid of melting point 120° C.

Specific rotation: −24.7° (c=3.0 in chloroform)

13C-NMR (50 MHz, CDCl$_3$) d=17.3 (d, J=30 Hz), 23.2, 24.2, 26.0, 27.7 (d, J=1.2 Hz), 32.7 (dd, J=10.7 and 30.9 Hz), 32.8, 35.7 (d, J=2.1 Hz), 38.2, 40.6, 48.0 (q, J=4.0 Hz)

EXAMPLE 2

Preparation of (−)-1,4-bis(cis-dimyrtanylphosphino)butane-bisborane Complex

The (−)-1,4-bis(cis-dimyrtanylphosphino)butane-bisborane complex was prepared in a similar manner to Example 1.

0.52 g (2 mmol) of 1,4-bis(dichlorophosphino)butane were added dropwise at 0° C. to a solution of 6.61 g (6.0 mmol) of di(cis-myrtanyl)zinc in 10 ml of THF. After addition was complete, the cooling bath was removed and the mixture was heated at 40° C. for 12 h. The reaction mixture was again cooled to 0° C. and treated with 6 ml (6 mmol) of a 1M solution of borane-dimethyl sulfide complex in methylene chloride. After 10 min at 0° C., the solvent was removed and the residue was flash chromatographed. 1.02 g of the phosphine-borane complex were isolated as a white solid.

Specific rotation: −40.2° (c=3.00 in chloroform). 1H-NMR (200 MHz, CDCl$_3$) d=0.95 (d, J=10.2 Hz, 4H), 1.02 (s, 12 H), 1.16 (s, 12H), 1.30–1.65 (m, 8H), 1.60–1.96 (m, 28H), 1.96–2.10 (m, 4H), 2.20–2.30 (m, 8H)

Decomplexation to give the free phosphine was achieved by adding diethylamine several times and distilling off the volatile constituents.

EXAMPLE 3

Preparation of tris(cis-myrtanyl)phosphine

It was possible to prepare, for example, tris(cis-myrtanyl)phosphine from beta-pinene and phosphorus trichloride in a similar manner. In the 1H-NMR spectrum (200 MHz, CDCl$_3$) the borane complex of this phosphine shows d=0.88 (d, J=9.8 Hz, 3H), 0.96 (s, 9H), 1.13 (s, 9H), 1.43 (m, 3H), 1.66 (m, 8H); 1.84 (m, 12H), 2.10 (m, 3H), 2.23 (m, 6H).

EXAMPLE 4

Applications of the Phosphines for Hydrogenation 3.0 mg of p-cymene-ruthenium chloride dimer (Aldrich) in 20 ml of methanol were initially introduced into a 200 ml laboratory autoclave with a glass liner from Roth and treated with 6.4 mg of (−)-1,2-bis(cis-dimyrtanylphosphino)ethane. After stirring at room temperature for 15 min, 260 mg (2.0 mmol) of ethyl acetoacetate were added to the yellow catalyst solution prepared in this way.

The autoclave was closed and the mixture was hydrogenated for 12 h at a hydrogen pressure of 100 bar and a temperature of 50° C. After letting down the autoclave, the reaction mixture was freed from the solvent and the residue was distilled in a bulb tube. 220 mg of ethyl (R)-3-hydroxybutanoate having a specific rotation of −34° C. (c=1, chloroform) were obtained. This corresponds to an enantiomeric excess of 74%.

EXAMPLE 5

Application of the Phosphines in Hydrogenation 3.0 mg of p-cymene-ruthenium chloride dimer (Aldrich) in 20 ml of methanol were initially introduced into a 200 ml laboratory autoclave having a glass liner from Roth and the mixture was treated with 6.4 mg of (−)-1,2-bis(cis-dimyrtanylphosphino)ethane. After stirring at RT for 15 min, 296 mg (2.0 mmol) of trans-2-methyl-3-phenyl-2-propen-1-ol were added to the yellow catalyst solution prepared in this way. The autoclave was closed and the mixture was hydrogenated for 12 hours at a hydrogen pressure of 100 bar and a temperature of 50° C. After letting down the autoclave, the reaction mixture was freed from the solvent and the residue was distilled in a bulb tube.

230 mg of 2-methyl-3-phenyl-2-propan-1-ol were obtained. The ee value is 76% ((R)-(−)-(9-anthryl),2,2,2-trifluoroethanol as NMR shift reagent)

EXAMPLE 6

Application of the Phosphines in Hydroformylation 3.90 mg of rhodium biscyclooctadiene tetrafluoroborate in 20 ml of benzene were initially introduced into a 200 ml laboratory autoclave having a glass liner from Roth and treated with 6.4 mg of (−)-1,2-bis(cis-dimyrtanylphosphino) ethane. After stirring at RT for 15 min, 236 mg (2.0 mmol) of alpha-methylstyrene were added to the yellow catalyst solution prepared in this way. After injecting 100 bar of a 1:1 mixture of hydrogen and carbon monoxide, the mixture was stirred for 24 h at 50° C. After opening the autoclave, the reaction mixture was filtered through 2×2 cm of alumina and the filtrate was freed from the solvent. 200 mg of a mixture of 3-phenylbutan-1-al and 2-phenyl-2-methylpropan-1-al in the ratio 80:20 (1H-NMR) were obtained. The enantiomeric excess of the 3-phenylbutan-1-al is 65%, determined by measurement of the NMR shift after reduction to the corresponding alcohol using NaBH$_4$.

EXAMPLE 7

Application of the Phosphines in the Isomerization of Allylamines 3.90 mg of rhodium biscyclooctadiene tetrafluoroborate in 20 ml of THF were initially introduced into a 200 ml laboratory autoclave having a glass liner from Roth and treated with 6.4 mg of (−)-1,2-bis(cis-dimyrtanylphosphino) ethane. After stirring at RT for 15 min, 306 mg (2.0 mmol) of geranylamine (Aldrich) were added to the yellow catalyst suspension prepared in this way. After injecting 2 bar of argon, the mixture was stirred for 24 h at 50° C. After opening the autoclave, the reaction mixture was filtered through 2×2 cm of alumina and the filtrate was freed from the solvent. The crude product was taken up in 10 ml of 30% acetic acid in water, stirred for 30 min at RT, then extracted three times with 30 ml of n-hexane in each time. The combined organic phases were dried over sodium sulfate and freed from the solvent under reduced pressure.

270 mg of citronellal were obtained as a colorless oil. The enantiomeric excess is 72% and the specific rotation −12.5° (neat).

We claim:

1. An optically active phosphine of the formula II

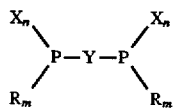

II where the variables have the following meanings:

X is an optically active terpene radical,

R is an unsubstituted or substituted phenyl radical,

Y is a bridge member having 1–10 C atoms in the formula I n is 1,2 or 3 and m is 0,1 or 2 with the proviso that n+m=3 in the formula II n is 1 or 2 and m is 0 or 1 with the proviso that n+m=2.

2. A phosphine as defined in claim 1, wherein X is a radical from the group which is formed from (+)-alpha-pinene, (−)-alpha-pinene, (+)-beta-pinene, (−)-beta-pinene, (+)-delta2-carene, (+)-delta3-carene, (+)-menthene, (+)- and (−)-camphene, (+)-fenchene, (+)- and (−)-limonene, (+)-menthadiene and (+)-longifolene.

3. A process for preparing optically active phosphines, which comprises a) hydroborating an optically active olefin, b) reacting the reaction product from step a) with a dialkylzinc compound, c) reacting the reaction product from step b) with a phosphorus halide to give the phosphine.

4. A process as defined in claim 3, wherein the optically active olefin used in step a) is a member of the group consisting of (+)-alpha-pinene, (−)-alpha-pinene, (+)-beta-pinene, (−)-beta-pinene, (+)-delta2-carene, (+)-delta3-carene, (+)-menthene, (+)- and (−)-camphene, (+)-fenchene, (+)- and (−)-limonene, (+)-menthadiene and (+)-longifolene.

5. A transition metal complex of the general formula IV

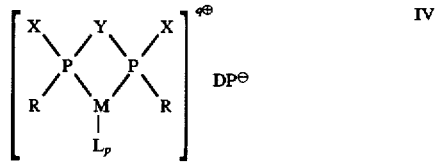

IV where the variables X, Y, R, m and n have the meanings mentioned in claim 1 and the other variables have the following meanings:

D is the equivalent of a noncoordinated anion,

L is an organic ligand,

M is a transition metal, p is 0 to 4 and q is 0 to 4.

6. A transition metal complex as defined in claim 5, wherein M is a metal from the group consisting of Ru, Rh and Ir.

7. A process for preparing the transition metal complexes as defined in claim 6, which comprises reacting a compound II with a transition metal compound V

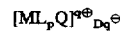

where Q is a leaving group.

8. A process for producing transition metal complexes which comprises reacting a phosphine of the formula II as defined in claim 1 with a dialkylzinc compound.

9. In a process which comprises asymmetric hydrogenation, the improvement which consists of employing as catalyst the transition metal complexes III

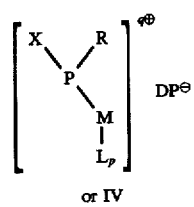
or IV
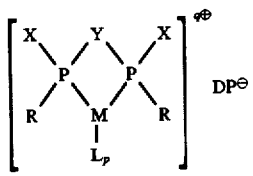
10. In a process which comprises asymmetric hydroformylation, the improvement which consists of employing as catalyst the transition metal complexes III
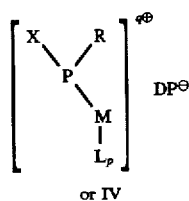
or IV
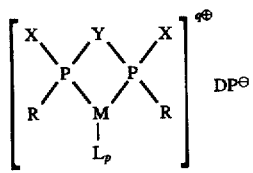
11. In a process which comprises asymmetrically isomerizing an allylamine to an enamine, the improvement which consists of employing as catalyst the transition metal complexes III
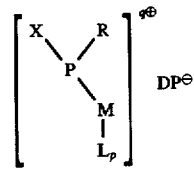
or IV
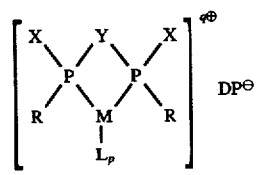
* * * * *